(12) United States Patent
Takeuchi

(10) Patent No.: US 8,911,355 B2
(45) Date of Patent: Dec. 16, 2014

(54) ENDOSCOPE

(71) Applicant: Olympus Medical Systems Corp., Tokyo (JP)

(72) Inventor: Yasuo Takeuchi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/864,401

(22) Filed: Apr. 17, 2013

(65) Prior Publication Data

US 2013/0274550 A1 Oct. 17, 2013

Related U.S. Application Data

(63) Continuation of application No. PCT/JP2012/078481, filed on Nov. 2, 2012.

(30) Foreign Application Priority Data

Nov. 25, 2011 (JP) .................................. 2011-257822

(51) Int. Cl.
*A61B 1/00* (2006.01)
*A61B 1/015* (2006.01)
*F16L 47/04* (2006.01)
*F16L 47/32* (2006.01)
*A61B 1/018* (2006.01)
*F16L 19/02* (2006.01)
*A61B 1/04* (2006.01)

(52) U.S. Cl.
CPC ................. *A61B 1/018* (2013.01); *A61B 1/015* (2013.01); *F16L 47/04* (2013.01); *A61B 1/0011* (2013.01); *A61B 1/00128* (2013.01); *F16L 47/32* (2013.01); *F16L 19/0243* (2013.01)
USPC ............................ 600/104; 600/130; 600/153

(58) Field of Classification Search
CPC ...... A61B 1/012; A61B 1/018; A61B 1/0011; A61B 1/00137
USPC ........... 600/130, 104, 128, 153–159; 128/912
See application file for complete search history.

(56) References Cited

U.S. PATENT DOCUMENTS 5,667,477 A * 9/1997 Segawa .......................... 600/153
5,735,793 A 4/1998 Takahashi et al.
(Continued)

FOREIGN PATENT DOCUMENTS

EP 2 517 615 A1 10/2012
JP 59-24585 A 2/1984
(Continued)

OTHER PUBLICATIONS

Extended Supplementary European Search Report dated Jun. 3, 2014 from related European Application No. 12 85 1504.6.

*Primary Examiner* — Alireza Nia
*Assistant Examiner* — Timothy J Neal
(74) *Attorney, Agent, or Firm* — Scully, Scott, Murphy & Presser, P.C.

(57) ABSTRACT

An endoscope includes a tube having a single layer structure or a laminated structure made up of a plurality of layers, a branching member that branches a tubular path in an endoscope operation section and has a tube connection section to which the tube is connected, a channel locking member that sandwiches the tube with the tube connection section to thereby fix the tube to the branching member in close contact, and a fastening member that presses and brings into close contact the tube sandwiched between the tube connection section and the channel locking member, in which the channel locking member is formed so as to have a tapered portion that covers an outer circumference of the tube and have at least one flat surface on an outer circumferential face of the tapered portion.

5 Claims, 6 Drawing Sheets

(56) References Cited

U.S. PATENT DOCUMENTS

| | | | |
|---|---|---|---|
| 6,569,087 B2 * | 5/2003 | Naito et al. | 600/156 |
| 7,029,436 B2 * | 4/2006 | Iizuka et al. | 600/160 |
| 7,371,211 B2 * | 5/2008 | Akiba | 600/156 |
| 8,454,501 B2 * | 6/2013 | Fernandez et al. | 600/182 |
| 2012/0172667 A1 * | 7/2012 | Takeuchi | 600/140 |

FOREIGN PATENT DOCUMENTS

| | | |
|---|---|---|
| JP | 2-63804 A | 5/1990 |
| JP | 3-57590 A | 6/1991 |
| JP | 3-130493 A | 12/1991 |
| JP | 4-44591 A | 4/1992 |
| JP | 5-34388 U | 5/1993 |
| JP | 9-229258 A | 9/1997 |
| JP | 10-108830 A | 4/1998 |
| JP | 2000-356291 A | 12/2000 |
| JP | 2006-26248 A | 2/2006 |
| JP | 2007-309503 A | 11/2007 |
| WO | 2012/005124 A1 | 1/2012 |

* cited by examiner

ENDOSCOPE

CROSS REFERENCE TO RELATED APPLICATION

This application is a continuation application of PCT/JP2012/078481 filed on Nov. 2, 2012 and claims benefit of Japanese Application No. 2011-257822 filed in Japan on Nov. 25, 2011, the entire contents of which are incorporated herein by this reference.

BACKGROUND OF THE INVENTION

1. Field of the Invention

The present invention relates to a connection structure of a tube arranged in an operation section of an endoscope.

2. Description of the Related Art

Conventionally, endoscopes have been commercialized which are equipped with an insertion portion provided with observation means such as an image pickup device and an ultrasound transducer at a distal end portion and formed in an elongated tubular shape, and an operation section provided with various operation members to which a proximal end of the insertion portion is connected. Among such types of endoscopes, a variety of medical endoscopes are being commercialized and becoming widespread, which are configured to insert the insertion portion into a body cavity of a living body of a patient or the like, acquire an observation image by the observation means, and be able to perform various inspections or treatments on a region such as a lesion in the body cavity of the living body while observing the region using the observation image.

There are various modes of such conventional endoscopes such as one whose insertion portion is introduced from the oral cavity, anus, urethra opening or the like or one whose insertion portion is introduced into the abdominal cavity from a through hole punctured in the body wall in the vicinity of the umbilical region in order to observe the interior of organs which are tubular cavities and tubes in the body, for example, a digestive system organ such as esophagus, stomach, large intestine, duodenum, a urinary system organ such as urethra, ureter, bladder or a respiratory system organ such as trachea, lung.

Furthermore, conventional endoscopes are provided with a treatment instrument insertion channel through which various treatment instruments or the like inserted from a treatment instrument insertion port provided at the operation section can be inserted, and which is made up of an elongated tubular body connected to an air/water feeding apparatus or a suction apparatus connected to the operation section. This treatment instrument insertion channel is inserted and arranged in the insertion portion, has an opening at a distal end portion thereof, and a proximal end portion thereof is connected to a connection member made of a metal member provided in the operation section. This connection member is interposed between the treatment instrument insertion port and the treatment instrument insertion channel and is configured to insert or withdraw the various treatment instruments introduced from the treatment instrument insertion port so as to be able to insert or withdraw the distal end of the treatment instrument from an opening at the distal end of the insertion portion. Furthermore, an air/water feeding tube that extends from the air/water feeding apparatus or a suction tube that extends from the suction apparatus is connected to the connection member.

In the conventional endoscope having such a configuration, the connection member functions as a branching member that branches a tubular path of the treatment instrument insertion channel into a tubular path from the treatment instrument insertion port and a tubular path from the air/water feeding or suction tube. In this way, it is possible to perform treatment on a lesion using the treatment instrument, collect a tissue of the lesion to conduct a biopsy for examining mucous membrane, secretion or the like, and at the same time to send a gas or liquid into the body cavity or perform suction from within the body cavity using the air/water feeding apparatus.

Furthermore, since high resistance is required in recent years as a treatment instrument insertion channel tube used for an endoscope, there is a case where in addition to a tube having a general single layer structure, a tube having a laminated structure such as a tube with a plurality of layers containing elemental wires, for example, a three-layer structure (inner resin layer, net wire layer (intermediate layer) and outer resin layer) is used. Furthermore, in consideration of chemical resistance or the like, and for a reduction of friction with the treatment instrument inserted therein, it is desirable to apply fluorine resin (polytetrafluoroethylene (PTFE)) as a raw material of the inner resin layer. In this case, a resin material other than fluorine resin is used for the raw material of the outer resin layer.

Water tightness or air tightness is preferably secured in a connection region between the connection member (branching member) made of a metal member and the treatment instrument insertion channel tube.

As means for water-tightly or air-tightly connecting the connection region between the metal member and the resin tube, various means are proposed or commercialized such as means disclosed in Japanese Patent Application Laid-Open Publication No. 2000-356291.

The means disclosed in Japanese Patent Application Laid-Open Publication No. 2000-356291 is designed to clamp one end of a tube connected to a tapered resin fastening device by pinching it using a nut-shaped tightening instrument and thus water-tightly connect and hold both parts. As an application example of this means, a connection member that connects a tap water hose and a metal faucet is illustrated.

Furthermore, as other means, means disclosed, for example, in Japanese Patent Application Laid-Open Publication No. 9-229258 is proposed.

The means described in Japanese Patent Application Laid-Open Publication No. 9-229258 is designed to interpose a split ring made of fluorine-based resin (raw material with a low frictional coefficient) between a fastening device and a tapered part when clamping one end of a tube connected to a tapered fastening device by pinching it using a nut-shaped tightening tool.

SUMMARY OF THE INVENTION

An endoscope according to an aspect of the present invention includes a tube having a single layer structure or a laminated structure including a plurality of layers, a branching member that branches a tubular path in an endoscope operation section and has a tube connection section to which the tube is connected, a channel locking member that sandwiches the tube with the tube connection section and thereby tightly fixes the tube to the branching member, and a fastening member that presses and brings into close contact the tube sandwiched between the tube connection section of the branching member and the channel locking member, in which the channel locking member includes a tapered portion that covers an outer circumference of the tube and is formed so as to have at least one flat surface on an outer circumferential face of the tapered portion.

An endoscope according to another aspect of the present invention includes a tube having a single layer structure or a laminated structure including a plurality of layers, a branching member that branches a tubular path in an endoscope operation section and has a tube connection section to which the tube is connected, a channel locking member that sandwiches the tube with the tube connection section and thereby tightly fixes the tube to the branching member, and a fastening member that pushes the channel locking member to press and bring into close contact the tube sandwiched between the tube connection section of the branching member and the channel locking member, in which a friction reducing member is arranged on a contact surface of either one of the channel locking member and the fastening member, both members coming into contact with each other on the contact surface.

DETAILED DESCRIPTION OF THE PREFERRED EMBODIMENTS

Figure 1:
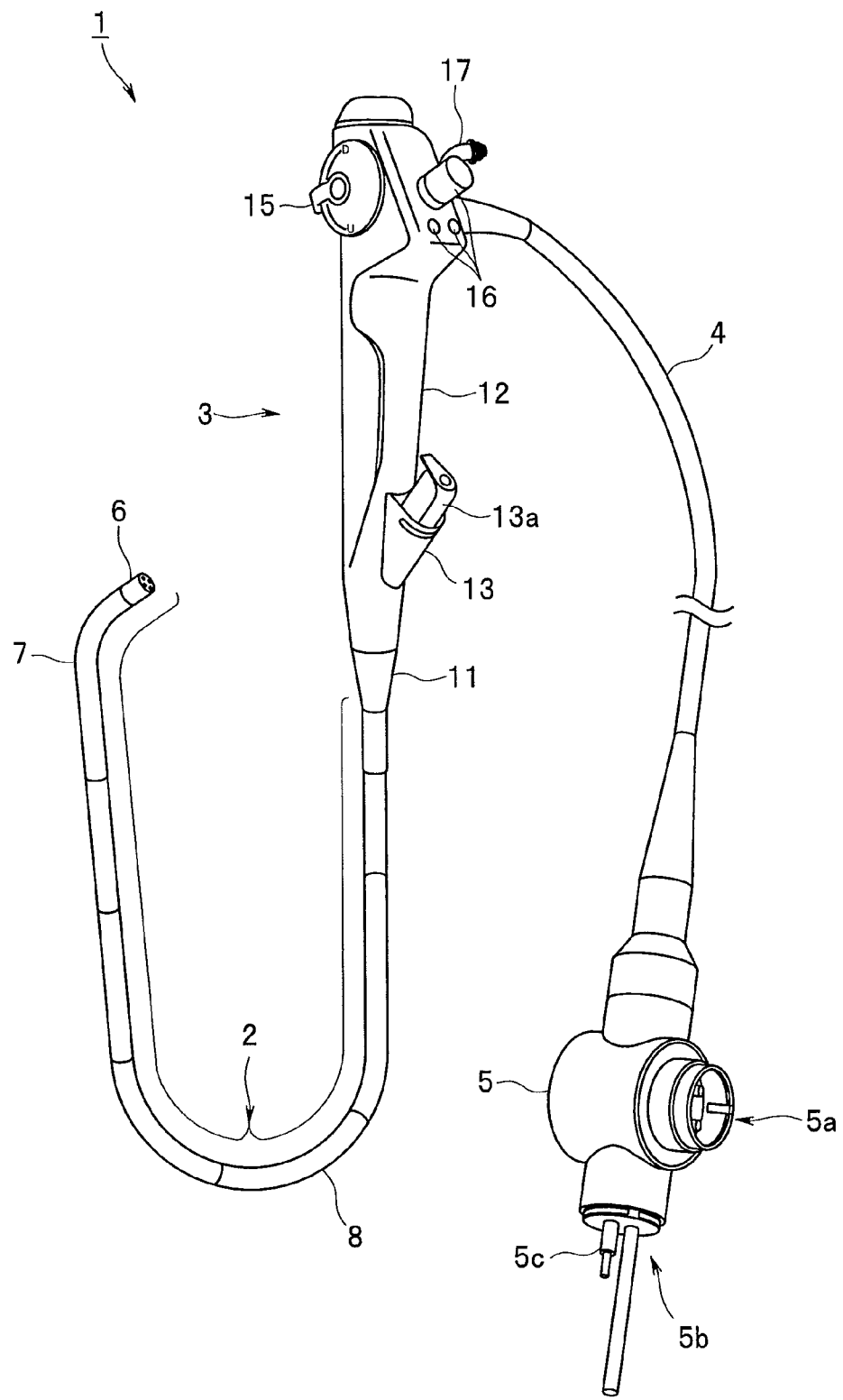
FIG. 1 is an overall perspective view illustrating an overall configuration of an endoscope according to a first embodiment of the present invention.

Hereinafter, the present invention will be described using embodiments illustrated in the accompanying drawings. Note that, in the respective drawings used in the following description, the respective components may be shown in scales varying from one component to another to illustrate the respective components in sizes they are recognizable in the drawings. Therefore, the quantity of the components, shapes of the components, size ratio among the components and relative positional relationships among the components in the present invention are not exclusively limited to the illustrated aspects.

First Embodiment

Figure 2:
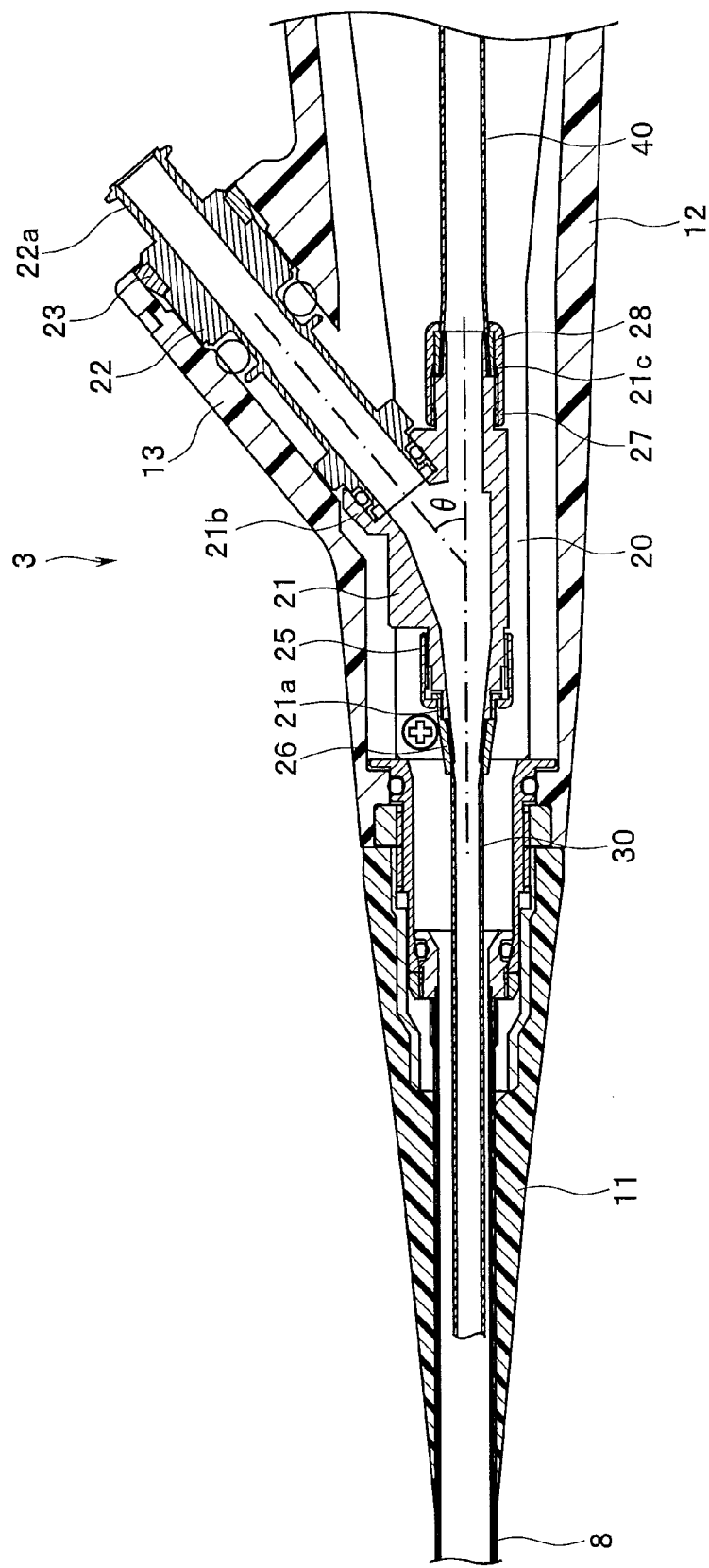
FIG. 2 is a cross-sectional view illustrating an internal configuration of an operation section of the endoscope in FIG. 1.
Figure 3:
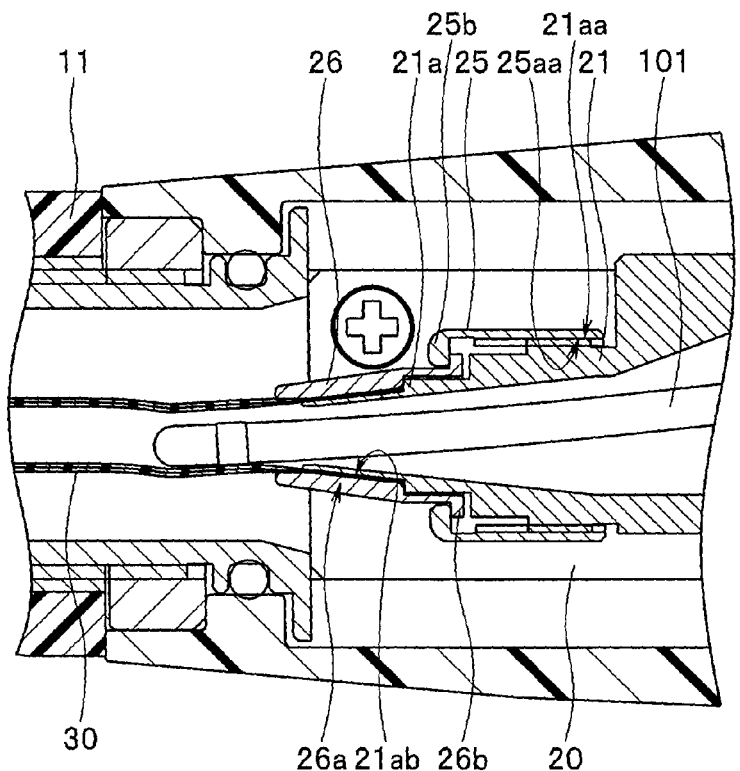
FIG. 3 is a principal part enlarged cross-sectional view showing an enlarged view of part of FIG. 2 (a vicinity of a connection region between a treatment instrument insertion channel and a branching member)
Figure 4:
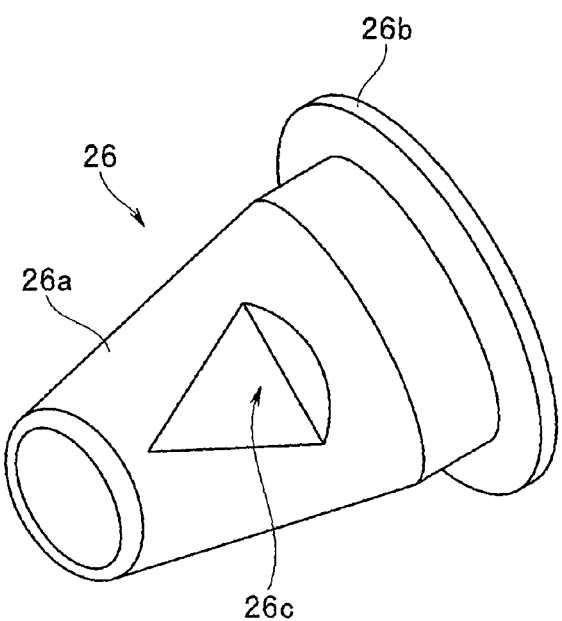
FIG. 4 is a perspective view of a tapered tube when extracted singly, applied to the endoscope in FIG. 1.
Figure 5:
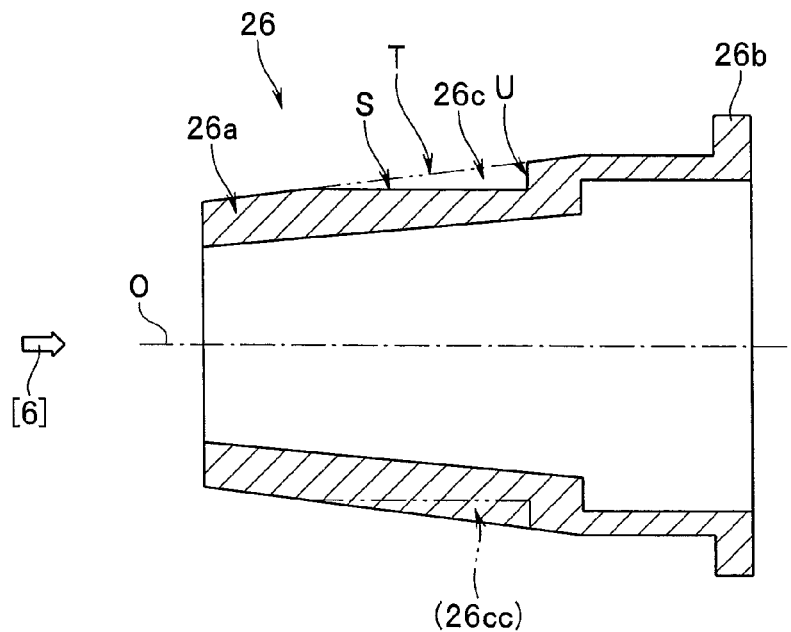
FIG. 5 is a cross-sectional view of the tapered tube in FIG. 4.
Figure 6:
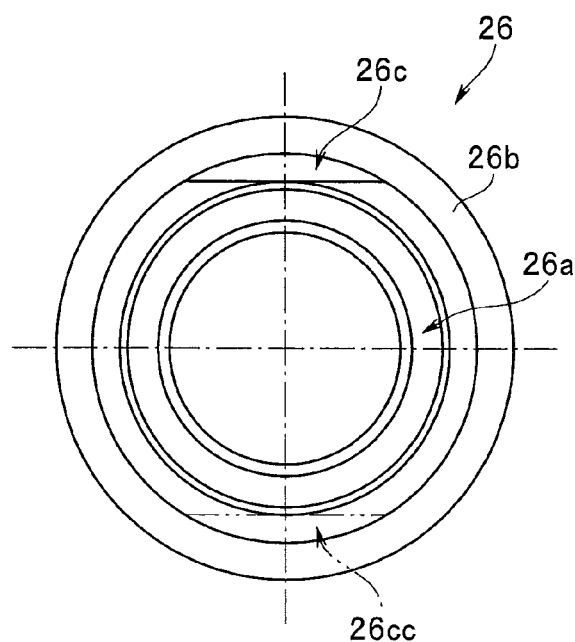
FIG. 6 is a front view of the tapered tube in FIG. 5 when viewed from the direction indicated by an arrow [6]
Figure 7:
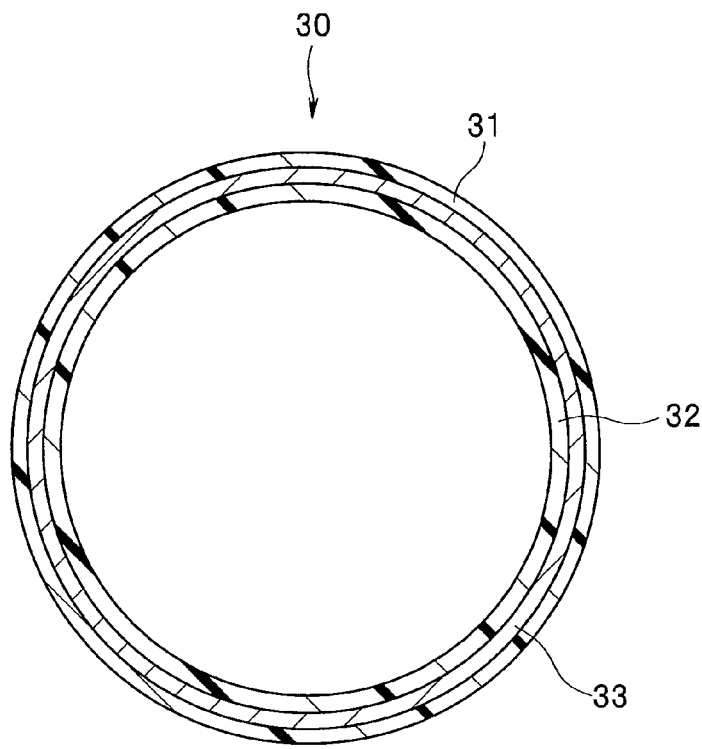
FIG. 7 is a cross-sectional view of a channel tube in a treatment instrument layer applied to the endoscope in FIG. 1.

FIG. 1 to FIG. 7 are diagrams illustrating a first embodiment of the present invention. Among them, FIG. 1 is an overall perspective view illustrating an overall configuration of an endoscope according to the first embodiment of the present invention. FIG. 2 is a cross-sectional view illustrating an internal configuration of an operation section of the endoscope of the present embodiment. FIG. 3 is a principal part enlarged cross-sectional view showing an enlarged view of part of FIG. 2 (a vicinity of a connection region between a treatment instrument insertion channel and a branching member). FIG. 4 is a perspective view of a tapered tube when extracted singly, applied to the endoscope of the present embodiment. FIG. 5 is a cross-sectional view of the tapered tube in FIG. 4. FIG. 6 is a front view of the tapered tube in FIG. 5 when viewed from the direction indicated by an arrow [6]. FIG. 7 is a cross-sectional view of a channel tube in a treatment instrument layer applied to the endoscope of the present embodiment.

As shown in FIG. 1, an endoscope 1 of the present embodiment is principally constructed of an insertion portion 2 formed into a shape like an elongated tube, an operation section 3 connected to a proximal end of this insertion portion 2, a universal cord 4 that extends from this operation section 3, and an endoscope connector 5 disposed at a distal end of the universal cord 4 or the like.

The insertion portion 2 is a flexible tubular member formed by connecting a distal end portion 6, a bending portion 7, and a flexible tube portion 8 in that order from the distal end. Of these members, the distal end portion 6 contains image pickup means, illumination means or the like therein.

The bending portion 7 is a mechanism region configured to be actively bendable in two up/down (UP-DOWN) directions through a rotation operation of a bending lever 15, which will be described later, among operation members of the operation section 3. Note that the bending portion 7 is not limited to this type, but may also be of a type bendable in four directions (all-round direction around an axis through vertical and horizontal operations) including left/right directions in addition to up/down directions.

The flexible tube portion 8 is a tubular member formed with flexibility so as to be passively bendable. This flexible tube portion 8 allows to be inserted thereinthrough not only a treatment instrument insertion channel (details will be described later), but also various signal lines that connect the image pickup means and illumination means of the distal end portion 6, and the operation section 3, and extend from the operation section 3 to the inside of the universal cord 4, and a light guide (not shown) that guides illuminating light from a light source apparatus (not shown), which will be described later, and causes the light to exit from the distal end portion 6.

The operation section 3 is configured by including a bend preventing portion 11 that is provided on the distal end side to cover a proximal end of the flexible tube portion 8 and is connected to the flexible tube portion 8, a grasping portion 12 that is connected to the bend preventing portion 11 and is grasped by the user's hand to operate the endoscope 1, various operation members (details will be described later, reference numerals 15 and 16 or the like) provided on the outer surface of the grasping portion 12, a treatment instrument insertion section 13 and a suction valve 17 or the like.

Examples of the operation members provided in the operation section 3 include the bending lever 15 that performs bending operation of the above-described bending portion 7, and a plurality of operation members 16 for performing air/water feeding operation or suction operation or operations corresponding to the image pickup means, illumination means or the like.

The treatment instrument insertion section 13 is provided with a treatment instrument insertion port for inserting various treatment instruments (not shown) and is a component that communicates with a treatment instrument insertion channel tube 30 inside the operation section 3 via a branching member 21 (see FIG. 2 and FIG. 3) which will be described later. This treatment instrument insertion section 13 is provided with a forceps plug 13a which is a cover member to open/close the treatment instrument insertion port and configured to be detachable (replaceable) from the treatment instrument insertion section 13.

The universal cord 4 is a composite cable that allows to insert therethrough, the above-described various signal lines that are inserted into the insertion portion 2 from the distal end portion 6 of the insertion portion 2 to the operation section 3 and extend from the operation section 3, the light guide of the light source apparatus (not shown), and an air/water feeding tube that extends out of the air/water feeding apparatus (not shown).

The endoscope connector 5 is configured by including an electric connector portion 5a on a side portion thereof to which an electric cable (not shown) for connection with a video processor (not shown) is connected, a light source connector portion 5b to which an optical fiber cable and an electric cable (not shown) for connection with the light source apparatus (not shown) are connected, and an air/water feeding plug 5c that connects the air/water feeding tube (not shown) from the air/water feeding apparatus (not shown) or the like.

Next, an internal configuration of the operation section 3 in the endoscope 1 of the present embodiment will be described using FIG. 2 to FIG. 7.

A fixing plate 20 is arranged in an inner space of the grasping portion 12 of the operation section 3 and a branching member 21 is fixed to the fixing plate 20.

The branching member 21 is a metal block body that has openings at both ends in a direction along the axis of the operation section 3 and at a protruding end inclined toward the treatment instrument insertion section 13 having a predetermined angle θ with respect to the axis connecting both ends.

That is, the branching member 21 is formed of a forward tube connection section 21a having a forward opening, a shaft connection section 21b that diagonally protrudes from one side toward the rear and has an opening at a distal end thereof, and a rear tube connection section 21c that has a rearward opening, and the respective connection sections (21a, 21b and 21c) communicate with each other through tubular paths formed inside.

A treatment instrument insertion channel tube 30 is connected to the forward tube connection section 21a. An insertion shaft 22 of the treatment instrument insertion section 13 is connected to the shaft connection section 21b. An air/water feeding or suction tube 40 is connected to the rear tube connection section 21c.

The insertion shaft 22 which is a tubular metal member is arranged inside the treatment instrument insertion section 13. One end of the insertion shaft 22 is connected to the shaft connection section 21b of the branching member 21 by means of insertion and engagement as described above. At the other end of the insertion shaft 22, a treatment instrument insertion pipe sleeve 22a is formed which constitutes a pipe sleeve through which the forceps plug 13a (see FIG. 1, but not shown in FIG. 2) can be inserted or removed. Note that this treatment instrument insertion pipe sleeve 22a is formed so as to slightly protrude outward from the treatment instrument insertion section 13 (that is, from a surface of the operation section 3). The insertion shaft 22 is fixed by a fixing ring 23 in the vicinity of the opening of the treatment instrument insertion section 13.

The forward tube connection section 21a is a tubular portion having a distal end tapered portion 21ab (see FIG. 3), having such a shape that the diameter of the distal end portion is smaller than the diameter of the proximal end portion, that is, a tapered shape, and is extrapolated and connected so that the inner circumferential face of the treatment instrument insertion channel tube 30 comes into close contact with the outer circumferential face thereof.

A male threaded portion 21aa (see FIG. 3) is formed on the outer circumferential side in the vicinity of the proximal end portion of the forward tube connection section 21a. A female thread 25aa (see FIG. 3) of a fastening ring 25 is screwed together with the male threaded portion 21aa. The fastening ring 25 is a fastening member made of a short cylindrical metal member formed by including an inward flange 25b on the front end side and the female thread 25aa on the rear end inner circumferential side.

A tapered tube 26 which is a channel locking member is connected on the distal end side of the fastening ring 25. The tapered tube 26 is a tubular metal member formed by including a tapered portion 26a whose distal end is tapered and an outward flange 26b at the rear end. Note that an angle of inclination of the tapered portion 26a of the tapered tube 26 is set so as to be substantially equivalent to the angle of inclination of the tapered portion of the forward tube connection section 21a.

The tapered portion 26a of the tapered tube 26 is inserted from the rear into the inner diameter portion of the inward flange 25b of the fastening ring 25, and the inward flange 25b of the fastening ring 25 comes into contact with the outward flange 26b of the tapered tube 26, forming one united body and configured to prevent the tapered tube 26 from dropping off the fastening ring 25. The fastening ring 25 and the tapered tube 26 united together in this way are attached to the forward tube connection section 21a with the treatment instrument insertion channel tube 30 inserted therein beforehand.

Furthermore, a notched portion 26c having a substantially flat shape obtained by cutting part of the tapered portion 26a as shown in FIG. 4, FIG. 5 and FIG. 6 is formed at a region on the outer circumferential face of the tapered tube 26. As shown in FIG. 5, this notched portion 26c is formed by removing an area defined by a region where a straight line S that extends parallel to a central axis O of the tapered tube 26 from a small diameter side of the tapered portion 26a toward the rear intersects with a straight line U that extends from a straight line T along an outer surface of the tapered portion 26a in a direction orthogonal to this straight line S. By forming the notched portion 26c on the outer surface of the tapered portion 26a of the tapered tube 26, the cross-sectional shape of a surface orthogonal to the axial direction of the notched portion 26c of the tapered portion 26a is formed in a shape different from a perfect circle.

Note that the present embodiment shows an example in FIG. 4 to FIG. 6 where one such notched portion 26c is formed, but without being limited to this example, it may also be possible to form a similar notched portion, for example, in a region denoted by a reference numeral 26cc shown by a two-dot dashed line in FIG. 5 and FIG. 6, that is, a region opposed to the notched portion 26c, a region halfway around the outer circumferential face of the tapered portion 26a so as to have two notched portions (26c and 26cc).

On the other hand, as shown in FIG. 2, a tapered portion is formed in the rear tube connection section 21c so as to have a small diameter at an end thereof. The air/water feeding or suction tube 40 is extrapolated and connected so that the inner circumferential face thereof comes into close contact with the outer circumferential face of the tapered portion of the rear tube connection section 21c. In this case, a fastening ring 27 containing a holding ring 28 is screwed with the rear tube connection section 21c. The holding ring 28 is a ring-shaped member arranged in a distal end inward flange of the rear tube connection section 21c.

Therefore, an end of the tube 40 is sandwiched between the tapered portion and the holding ring 28 of the rear tube connection section 21c. If the rear tube connection section 21c and the fastening ring 27 are screwed together in this condition, the distal end inward flange of the rear tube connection section 21c moves forward, that is, toward the branching member 21 together with the holding ring 28 that is in contact therewith in accordance with the amount of screwing. This causes the holding ring 28 to act on the tube 40 so as to crush it against the tapered portion of the rear tube connection section 21c to firmly fix and hold the tube 40.

Note that the treatment instrument insertion channel tube 30 is inserted and arranged in the bend preventing portion 11 of the operation section 3, and from the flexible tube portion 8 to the distal end portion 6, that is, throughout the whole length of the insertion portion 2. Furthermore, the air/water feeding or suction tube 40 has a configuration of being branched into two paths (not shown) inside the operation section 3: one toward the suction valve 17 side and the other in which the air/water feeding or suction tube 40 passes through the universal cord 4 up to the air/water feeding plug 5c.

In such a configuration, the branching member 21 made up of a metal member is interposed between the treatment instrument insertion section 13 and the treatment instrument insertion channel tube 30, and at the same time interposed between the air/water feeding or suction tube 40 and the treatment instrument insertion channel tube 30. Therefore, the branching member 21 functions as branch means for branching the tubular path of the treatment instrument insertion channel tube 30 into the tubular path from the treatment instrument insertion section 13 and the tubular path from the air/water feeding or suction tube 40.

On the other hand, a tubular member provided with high resistance and chemical resistance is used for the treatment instrument insertion channel tube 30. More specifically, as shown, for example, in FIG. 7, a multi-layer structure made up of a plurality of resin layers, that is, an inner resin layer 32, an outer resin layer 31 and a net wire layer 33 which is an intermediate layer formed of an elemental wire such as metal fiber woven between these two layers (a three-layer structure is illustrated in the present embodiment) is used for the treatment instrument insertion channel tube 30.

To reduce friction with a treatment instrument for the endoscope inserted therein (see reference numeral 101 in FIG. 3), a raw material such as fluorine resin (PTFE) is preferably used for the inner resin layer 32. Furthermore, in addition to the metal raw material, for example, carbon-based fiber such as acrylic fiber and non-metal raw material such as resin or non-metal mixed part (resin-mixed metal or the like) may be used for the net wire layer 33. A resin material other than fluorine resin is used for the outer resin layer 31 in consideration of adhesion with the inner resin layer 32. Assuming that the rest of the configuration is substantially the same as the configuration of conventional endoscopes, detailed descriptions thereof will be omitted.

In the endoscope 1 according to the present embodiment having the above configuration, in a step of assembling internal components of the operation section 3, the branching member 21 is connected to the treatment instrument insertion channel tube 30 as follows.

That is, the fastening ring 25 and the tapered tube 26 united together beforehand are inserted into the treatment instrument insertion channel tube 30. First, one end of the treatment instrument insertion channel tube 30 is connected to the distal end tapered portion 21ab of the forward tube connection section 21a of the branching member 21. In this case, the treatment instrument insertion channel tube 30 is extrapolated and connected so that the inner circumferential face thereof covers the outer circumferential face of the distal end tapered portion 21ab. In this case, both surfaces are in substantially close contact with each other.

Next, the female thread 25aa of the fastening ring 25 is screwed into the male threaded portion 21aa of the forward tube connection section 21a of the branching member 21. In this case, one end of the treatment instrument insertion channel tube 30 is sandwiched between the inner circumferential face of the tapered portion 26a of the tapered tube 26 and the outer circumferential face of the distal end tapered portion 21ab of the forward tube connection section 21a. The inward flange 25b of the fastening ring 25 is in contact with the outward flange 26b of the tapered tube 26.

When the fastening ring 25 is rotated in the fastening direction in this condition, the tapered tube 26 moves toward the rear side, that is, toward the branching member 21 side in accordance with the amount of screwing. Accompanying this movement, the fastening ring 25 acts on one end of the treatment instrument insertion channel tube 30 (sandwiched portion) so as to crush it against the distal end tapered portion 21ab of the forward tube connection section 21a. This causes the tube 30 to be firmly fixed and held in close contact.

In this case, if the fastening ring 25 is rotated in the fastening direction, the tapered tube 26 is also rotated in the same direction. Here, as described above, since a raw material other than fluorine resin, that is, a raw material whereby friction is not reduced is used for the outer resin layer 31 of the treatment instrument insertion channel tube 30, there is a possibility that the treatment instrument insertion channel tube 30 may also rotate simultaneously as the fastening ring 25 and the tapered tube 26 rotate.

Therefore, when the fastening ring 25 is rotated in the fastening direction, the outer circumferential face of the tapered tube 26 is grasped using a tool or the like so that the tapered tube 26 may not rotate. In this case, if the substantially flat surface of the notched portion 26c is pinched as the region of grasping the tapered tube 26 using a tool or the like, the tapered tube 26 can be reliably grasped, and it is thereby possible to easily prevent the tapered tube 26 from rotating simultaneously.

As described above, according to the first embodiment, since the notched portion 26c is provided on the tapered tube 26 and the outer circumferential cross section thereof is made to have a cross-sectional shape different from a perfect circle, when the fastening ring 25 is rotated in the fastening direction, if the tapered tube 26 is grasped using a tool or the like, it is reliably prevent the tapered tube 26 from rotating, and thereby suppress rotation of the tapered tube 26. Therefore, as a result, it is possible to prevent the treatment instrument insertion channel tube 30 from rotating simultaneously and reliably assemble the tube 30 without causing damage thereto.

Second Embodiment

Figure 8:
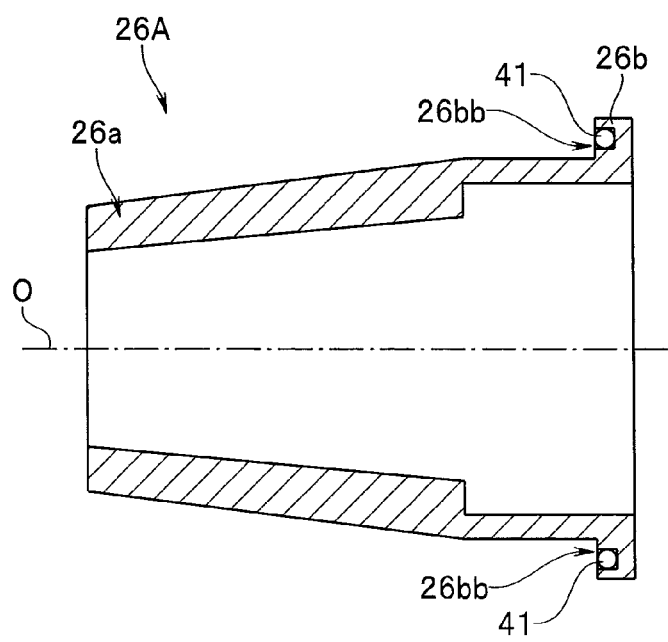
FIG. 8 is a cross-sectional view of a tapered tube applied to an endoscope according to a second embodiment of the present invention.

The above-described first embodiment has shown an example where the outer circumferential shape of the tapered tube 26 is designed to be a shape that facilitates grasping using a tool or the like. In contrast, a second embodiment of the present invention, which will be described below, designs a structure for preventing simultaneous rotation of the tapered tube itself. That is, FIG. 8 is a cross-sectional view of the tapered tube applied to an endoscope according to the second embodiment of the present invention. The basic configuration of the endoscope of the present embodiment is substantially the same as the aforementioned first embodiment, and differs only in the configuration of the tapered tube. Therefore, in the following description of the second embodiment, only components different from those of the aforementioned first embodiment will be described in detail. Note that, although illustration using drawings and description of the same components as those in the aforementioned first embodiment will be omitted, when the same components as those in the aforementioned first embodiment are included in the description as required, the same reference numerals used for the description of the above first embodiment will be used.

As shown in FIG. 8, a tapered tube 26A used for the endoscope of the present embodiment is provided with, for example, a plurality of ball bearings 41 on a contact surface 26bb where an outward flange 26b comes into contact with an inward flange (25b; see FIG. 3) of the fastening ring (25) when the tapered tube 26A is assembled at a predetermined region in the endoscope operation section.

The ball bearing 41 is a member for reducing friction between the outward flange 26b of the tapered tube 26A and the inward flange (25b) of the fastening ring (25) when both come into contact with each other. Thus, arranging the friction reducing member (e.g., ball bearing 41) on the tapered tube 26A reduces the frictional force between the outward flange 26b of the tapered tube 26A and the inward flange 25b of the fastening ring 25. Therefore, even when the fastening ring 25 is rotated, it is possible to prevent the rotation operation from causing the tapered tube 26A to rotate simultaneously. This also prevents the treatment instrument insertion channel tube 30 which is in close contact with the tapered tube 26A from rotating simultaneously.

As described so far, the configuration of the above-described second embodiment can also obtain the various effects described in the first embodiment. Furthermore, although the configuration of the aforementioned first embodiment requires a tool for assembly, in this regard, the tapered tube 26A in the present embodiment is provided with the ball bearing 41 as the friction reducing member, and it is thereby possible to prevent simultaneous rotation of the tapered tube 26A without using any tool or the like.

Note that the above-described second embodiment shows a configuration example in which the friction reducing member (e.g., a plurality of ball bearings 41) is arranged on the contact surface 26bb of the outward flange 26b of the tapered tube 26A, but without being limited to this configuration example, a configuration may be adopted in which a friction reducing member such as ball bearings is provided on a region opposed to and in contact with the contact surface 26bb of the outward flange 26b of the tapered tube 26A, that is, the inward flange (25b) side of the fastening ring (25). Effects quite similar to those in the above-described second embodiment can be obtained in this case, too.

Furthermore, the aforementioned first and second embodiments have shown an example in which a tube having a three-layer structure is used as the treatment instrument insertion channel tube 30, but the present invention is not limited to this example, and, for example, a tube having a single layer structure may also be used as long as it is made of a tubular member provided with high resistance and chemical resistance, and effects quite similar to those in the above-described first and second embodiments can be obtained in that case, too.

REFERENCE EXAMPLE

Note that as for the tube used for the treatment instrument insertion channel in the endoscope, even if the tube itself is damaged, a mechanism capable of detecting such abnormality is preferably provided in consideration of repair or the like.

As for the three-layer structure tube used for the endoscope of the aforementioned embodiment, in the event that only the inner layer or outer layer is damaged, the tube as a whole may not lose its function. Therefore, air leakage or the like may not be able to be detected in a water leakage check during an ordinarily conducted endoscope inspection. More specifically, even if only the inner layer is damaged and a hole is opened, for example, the outer layer member serves as a cover, and therefore even if a water leakage check is performed, the case may be judged as normal.

Figure 9:
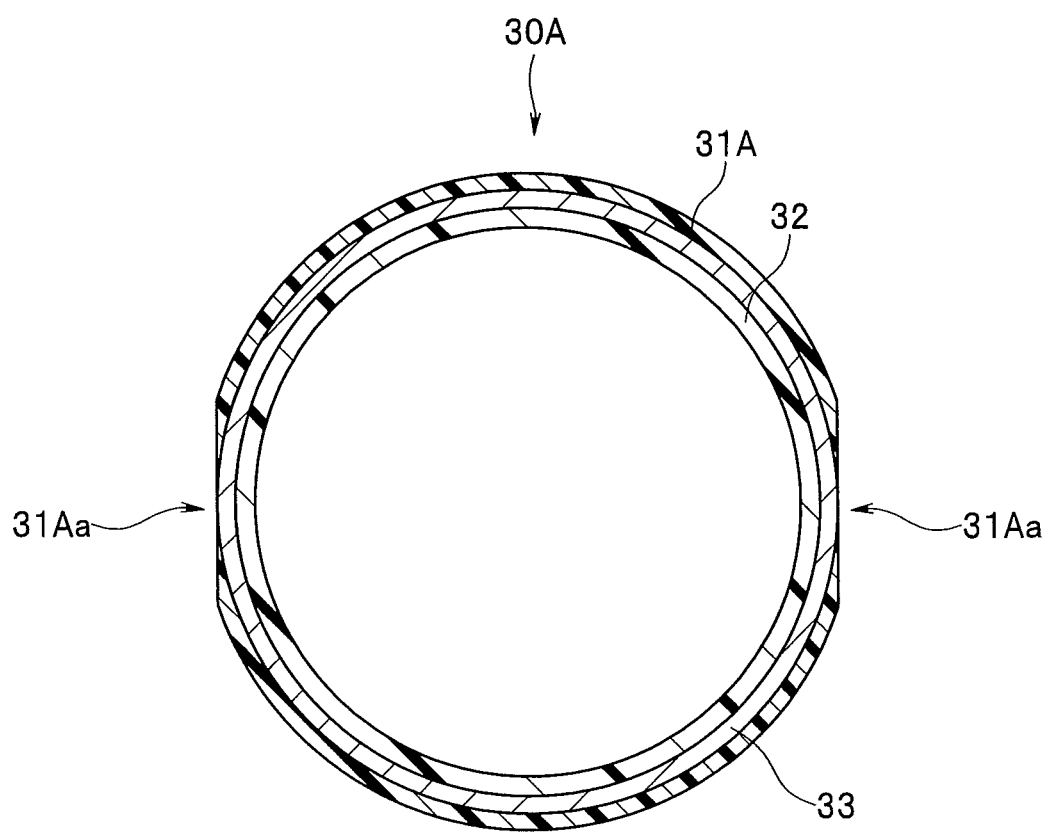
FIG. 9 is a cross-sectional view illustrating a tube structure according to a reference example of the present invention.

Even in such a case, it would be highly convenient if the structure is designed to be able to detect the abnormality. From this perspective, the following tube structure is disclosed. FIG. 9 is a cross-sectional view illustrating a tube structure according to the present reference example.

A tube 30A of the present reference example is formed into a three-layer structure including an inner resin layer 32, a net wire layer 33 which is an intermediate layer and an outer resin layer 31A as in the case of the tube 30 in the above respective embodiments.

The outer resin layer 31A has notched regions 31Aa obtained through partial notching from a circular shape so as to have a cross-sectional shape different from the circle. These notched regions 31Aa are formed such that part of the net wire layer 33 is exposed from part of the outer surface of the tube 30.

In this case, the inner layer, the net wire layer, and the outer layer are connected together by only a closely contacting force without any adhesive or the like among the layers or without using means such as welding among the layers.

In such a configuration, when the inner layer 32 is damaged, air may leak from the notched regions 31Aa via the net wire layer 33. Therefore, at the time of the water leakage check, it is possible to easily detect abnormality such as air leakage by applying an inner pressure equal to or greater than the closely contacting force among the respective layers.

Furthermore, since areas of contacts among the inner layer, the elemental wire and the outer layer are configured without welding or adhesion or the like, the air circulation channel can be reliably secured. Therefore, it is easier to detect abnormality such as air leakage attributable to damage of the inner layer or the outer layer.

The endoscope in the present reference example is a three-layer structure tube in which the inner layer is made of resin, the intermediate layer is made of elemental wire and the outer layer is made of resin, at least part of the outer layer resin is notched, part of the intermediate layer is exposed to the outside, contact surfaces between the inner layer resin and the intermediate net wire layer, and between the outer layer resin and the intermediate net wire layer are closely surface-contacted with each other and when the air pressure inside the tube becomes a surface contacting force or greater, the air in the tube is configured to emit to the outside of the outer layer resin.

Note that it goes without saying that the present invention is not limited to the aforementioned embodiments, but various modifications or applications can be made without departing from the scope and spirit of the present invention. Furthermore, the above embodiments include inventions in various stages, and the various inventions can be extracted depending on an appropriate combination of a plurality of disclosed configuration requirements. For example, even if some configuration requirements are deleted from all the configuration requirements disclosed in the above respective embodiments, as long as the problems to be solved by the invention can be solved and the effects of the invention can be obtained, the configuration from which these configuration requirements are deleted can be extracted as an invention.

The present invention is applicable not only to an endoscope control apparatus in the medical field but also to an endoscope control apparatus in the industrial field.

What is claimed is:

1. An endoscope comprising:
   a tube having a single layer structure or a laminated structure comprising a plurality of layers;
   a branching member that branches a tubular path in an endoscope operation section and has a tube connection section to which the tube is connected;
   a channel locking member that sandwiches the tube with the tube connection section and thereby tightly fixes the tube to the branching member; and
   a fastening member that presses and brings into close contact the tube sandwiched between the tube connection section of the branching member and the channel locking member,
   wherein the channel locking member comprises an inner tapered portion that covers an outer circumference of the tube and an outer tapered portion formed on an exterior surface of the channel locking member, the outer tapered portion being in parallel with the inner tapered portion, the channel locking member having at least one flat surface, the flat surface being substantially parallel to a central axis of the channel locking member, and the at least one flat surface being formed on the exterior surface such that a cross-sectional shape of a surface orthogonal to a central axis of the channel locking member is formed in a shape of an imperfect circle.

2. The endoscope according to claim 1, wherein the flat surface is formed on a notched portion formed by notching part of the tapered portion on the exterior surface.

3. The endoscope according to claim 2, wherein the notched portion of the tapered portion of the channel locking member is formed at two mutually opposing locations of the exterior surface.

4. The endoscope according to claim 1, further comprising a friction reducing member arranged on a contact surface of either one of the channel locking member and the fastening member, the channel locking member and the fastening member coming into contact with each other on the contact surface.

5. The endoscope according to claim 4, wherein the friction reducing member is a ball bearing.

* * * * *